United States Patent
Wu et al.

(10) Patent No.: US 12,298,655 B2
(45) Date of Patent: May 13, 2025

(54) PROJECTION SYSTEM AND PROJECTION METHOD

(71) Applicant: Coretronic Corporation, Hsin-Chu (TW)

(72) Inventors: Chia-Chien Wu, Hsin-Chu (TW); Kun-Chen Hsu, Hsin-Chu (TW); Shih Kang Lin, Hsin-Chu (TW)

(73) Assignee: Coretronic Corporation, Hsin-Chu (TW)

( * ) Notice: Subject to any disclaimer, the term of this patent is extended or adjusted under 35 U.S.C. 154(b) by 493 days.

(21) Appl. No.: 17/496,768

(22) Filed: Oct. 8, 2021

(65) Prior Publication Data

US 2022/0121098 A1    Apr. 21, 2022

Related U.S. Application Data

(60) Provisional application No. 63/093,795, filed on Oct. 20, 2020.

(30) Foreign Application Priority Data

May 28, 2021   (CN) .......................... 202110593656.9

(51) Int. Cl.
   *G03B 31/00*     (2021.01)
   *A61B 5/00*      (2006.01)
   (Continued)

(52) U.S. Cl.
   CPC ............ *G03B 31/00* (2013.01); *A61B 5/4809* (2013.01); *A61M 21/02* (2013.01); *G03B 21/14* (2013.01);
   (Continued)

(58) Field of Classification Search
   CPC ...... G03B 31/00; G03B 21/14; A61B 5/4809; A61B 2503/12; A61B 5/024;
   (Continued)

(56) References Cited

U.S. PATENT DOCUMENTS

2005/0200816 A1 *  9/2005  Hsu .................. G03B 21/16
                                                      353/57
2006/0142968 A1    6/2006  Jan et al.
   (Continued)

FOREIGN PATENT DOCUMENTS

CN    101773696    7/2010
CN    203809330    9/2014
   (Continued)

OTHER PUBLICATIONS

"Office Action of Taiwan Counterpart Application", issued on Nov. 14, 2023, p. 1-p. 14.
   (Continued)

*Primary Examiner* — Magda Cruz
(74) *Attorney, Agent, or Firm* — JCIPRNET

(57) ABSTRACT

The disclosure provides a projection system and a projection method. The projection system includes a projection device. The projection device includes a projection module, a controller, and an audio player. The controller is coupled to the projection module. The audio player is coupled to the controller. When the controller executes the prepare-for-sleep mode, the controller operates the projection module to dim a projection beam or to project a predetermined projection image and operates the audio player to play a predetermined sound.

30 Claims, 5 Drawing Sheets

(51) Int. Cl.
*A61M 21/02* (2006.01)
*G03B 21/14* (2006.01)
*G06F 3/16* (2006.01)
A61M 21/00 (2006.01)
G06F 3/01 (2006.01)
G08B 21/02 (2006.01)

(52) U.S. Cl.
CPC .......... *G06F 3/165* (2013.01); *A61B 2503/12* (2013.01); *A61M 2021/0027* (2013.01); *A61M 2021/005* (2013.01); *G06F 3/011* (2013.01); *G08B 21/02* (2013.01)

(58) Field of Classification Search
CPC ....... A61B 5/0816; A61B 5/163; A61B 5/369; A61B 5/4812; A61B 2560/0242; A61B 5/486; G06F 3/165; G06F 3/011; G08B 21/02; G08C 17/02; H05B 47/105; H05B 47/11; H05B 47/16; H05B 47/19; A61M 2021/0027; A61M 2021/0044; A61M 2021/005; A61M 2021/0083; A61M 2205/18; A61M 2205/3306; A61M 2205/3592; A61M 2205/50; A61M 2205/587; A61M 2210/0612; A61M 2230/06; A61M 2230/10; A61M 2230/30; A61M 2230/42; A61M 2230/63; A61M 21/02
USPC .......................................................... 353/15
See application file for complete search history.

(56) References Cited

U.S. PATENT DOCUMENTS

| | | | | |
|---|---|---|---|---|
| 2007/0242225 | A1* | 10/2007 | Bragg | G03B 31/04 352/12 |
| 2012/0188451 | A1* | 7/2012 | Schmidt | A63H 5/00 348/E9.025 |
| 2014/0316191 | A1 | 10/2014 | de Zambotti et al. | |
| 2014/0316192 | A1 | 10/2014 | de Zambotti et al. | |
| 2016/0151603 | A1* | 6/2016 | Shouldice | A61B 5/486 600/26 |
| 2016/0217672 | A1* | 7/2016 | Yoon | A61B 5/4818 |
| 2016/0317099 | A1 | 11/2016 | Kawai et al. | |
| 2016/0328533 | A1* | 11/2016 | Kawai | A61B 5/7271 |
| 2017/0031324 | A1* | 2/2017 | Toda | H05B 47/115 |
| 2017/0136348 | A1* | 5/2017 | Hattori | A61B 5/7271 |
| 2022/0121098 | A1 | 4/2022 | Wu et al. | |
| 2024/0163407 | A1 | 5/2024 | Tsui et al. | |

FOREIGN PATENT DOCUMENTS

| | | |
|---|---|---|
| CN | 105303770 | 2/2016 |
| CN | 206372374 | 8/2017 |
| CN | 107548474 | 1/2018 |
| CN | 107670158 | 2/2018 |
| CN | 108052012 | 5/2018 |
| CN | 108319461 | 7/2018 |
| CN | 108853679 | 11/2018 |
| CN | 109348196 | 2/2019 |
| CN | 110193127 | 9/2019 |
| CN | 110515293 | 11/2019 |
| CN | 110639113 | 1/2020 |
| CN | 110825449 | 2/2020 |
| CN | 211062439 | 7/2020 |
| CN | 112671623 | 8/2021 |
| CN | 114339334 | 4/2022 |
| EP | 3096235 | 11/2016 |
| EP | 3096238 | 11/2016 |
| EP | 3096288 | 11/2016 |
| JP | 2011255008 | 12/2011 |
| JP | 2017113453 | 6/2017 |
| JP | 2020054839 | 4/2020 |
| JP | 2022069353 | 5/2022 |
| TW | 200508773 | 3/2005 |
| TW | 202121146 | 6/2021 |

OTHER PUBLICATIONS

"Office Action of China Counterpart Application", issued on Nov. 28, 2023, p. 1-p. 11.

"Office Action of Taiwan Related Application, Application No. 112102494", issued on Nov. 13, 2023, p. 1-p. 7.

"Office Action of Taiwan Counterpart Application", issued on Jan. 27, 2022, p. 1-p. 12.

"Office Action of Taiwan Counterpart Application", issued on Feb. 19, 2024, p. 1-p. 14.

"Search Report of related Europe Counterpart Application No. 23207579.6", issued on Apr. 2, 2024, p. 1-p. 12.

Xia; Yiting et al., "Resting the Brain by Music: A Review of the Studies on Meditation Music", Explorations in Music, with English abstract, Oct. 15, 2020, pp. 87-91, vol. 4.

"Notice of allowance of China Counterpart Application", issued on Oct. 11, 2024, p. 1-p.4.

* cited by examiner

PROJECTION SYSTEM AND PROJECTION METHOD

CROSS-REFERENCE TO RELATED APPLICATION

This application claims the priority benefit of U.S. provisional application Ser. No. 63/093,795, filed on Oct. 20, 2020 and China application serial no. 202110593656.9, filed on May 28, 2021. The entirety of each of the above-mentioned patent applications is hereby incorporated by reference herein and made a part of this specification.

BACKGROUND

Technical Field

The disclosure relates to an audio-visual system, and more particularly to a projection system and a projection method.

Description of Related Art

Nowadays, entertainment electronic products have become an indispensable part of human life, and many people still use electronic products, such as mobile phones, TVs, or projectors until the last moment before going to bed. However, over-dependence on these electronic products not only delays the bedtime of the user but even results in insomnia. Moreover, after the user falls asleep, the display device of such electronic products may not be turned off, causing the display device to continue to operate. In other words, when such electronic products cannot be turned off automatically, it is not only easy to cause power waste but possible to interfere with the sleep of the user.

The information disclosed in this Background section is only for enhancement of understanding of the background of the described technology and therefore it may contain information that does not form the prior art that is already known to a person of ordinary skill in the art. Further, the information disclosed in the Background section does not mean that one or more problems to be resolved by one or more embodiments of the disclosure was acknowledged by a person of ordinary skill in the art.

SUMMARY

The disclosure provides a projection system and a projection method capable of working with the sleep behavior of a user to provide appropriate projection images and audio effects.

The projection system of the disclosure includes a projection device. The projection device includes a projection module, a controller, and an audio player. The controller is coupled to the projection module. The audio player is coupled to the controller. When the controller executes a prepare-for-sleep mode, the controller operates the projection module to dim a projection beam or to project a predetermined projection image and operates the audio player to play a predetermined sound.

The projection method of the disclosure is adapted for a projection system. The projection system includes a projection device. The projection device includes a projection module, a controller, and an audio player. The projection method includes the following steps. When the controller executes a prepare-for-sleep mode, the controller operates the projection module to dim a projection beam or to project a predetermined projection image, and the controller operates the audio player to play a predetermined sound.

Based on the above, with the projection system and projection method of the disclosure, the projection beam or the projection image may be automatically adjusted, and the audio effect may be automatically adjusted to create an audio-visual situation suitable for the user to prepare for sleep.

Other objectives, features and advantages of the disclosure will be further understood from the further technological features disclosed by the embodiments of the disclosure wherein there are shown and described preferred embodiments of this disclosure, simply by way of illustration of modes best suited to carry out the disclosure.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

In the following detailed description of the preferred embodiments, reference is made to the accompanying drawings which form a part hereof, and in which are shown by way of illustration specific embodiments in which the invention may be practiced. In this regard, directional terminology, such as "top", "bottom", "front", "back", "left", "right", etc., is used with reference to the orientation of the Figure(s) being described. Therefore, the used directional terminology is only intended to illustrate, rather than limit, the disclosure.

The components of the disclosure may be positioned in a number of different orientations. As such, the directional terminology is used for purposes of illustration and is in no way limiting. On the other hand, the drawings are only schematic and the sizes of components may be exaggerated for clarity.

It is to be understood that other embodiment may be utilized and structural changes may be made without departing from the scope of the disclosure. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "Coupled," and "mounted," and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component directly faces "B" component or one or more additional components are between "A" component and "B" component. Also, the description of "A" component "adjacent to" "B" component herein may contain the situations that "A" component is directly "adjacent to" "B" component or one or more additional components are between "A" component and "B" component. Accordingly, the drawings and descriptions will be regarded as illustrative in nature and not as restrictive.

Figure 1:
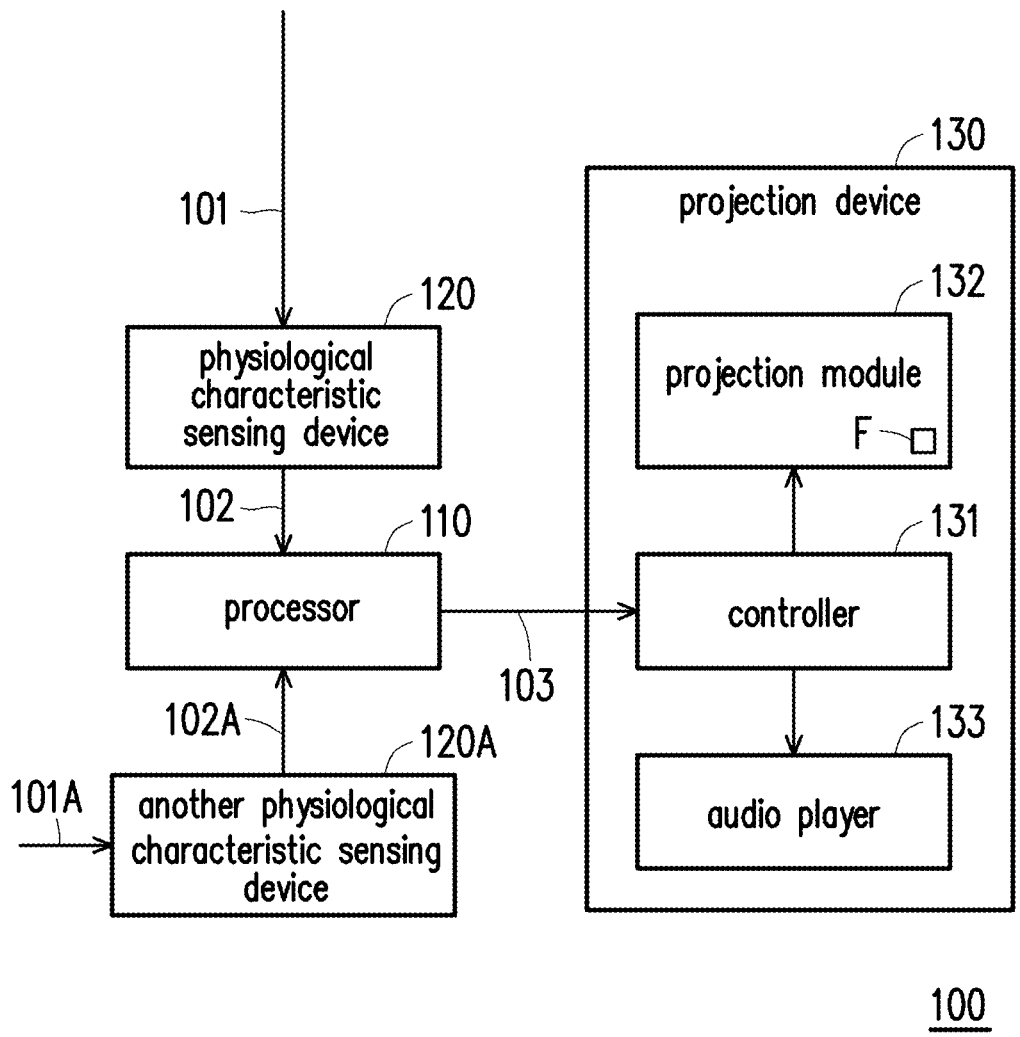
FIG. 1 is a schematic circuit view of a projection system according to an embodiment of the disclosure.

FIG. 1 is a schematic circuit view of a projection system according to an embodiment of the disclosure. Referring to FIG. 1, a projection system 100 includes a processor 110, a physiological characteristic sensing device 120, and a projection device 130. The processor 110 is coupled to (electrically connected to) the physiological characteristic sensing device 120 and the projection device 130. The projection device 130 includes a controller 131, a projection module 132, and an audio player 133. The controller 131 is coupled to the projection module 132, and the audio player 133. In the embodiment, the physiological characteristic sensing device 120 may obtain physiological information 101 of a sensed target (e.g., the user). The physiological information 101 may include information, such as heartbeat, respiratory rate, and/or blood pressure, but the disclosure is not limited thereto. The physiological characteristic sensing device 120 may output a corresponding physiological characteristic signal 102 to the processor 110 according to the physiological information 101, and for example, the physiological characteristic signal 102 may include at least one of a heartbeat signal, a pulse signal, an eye movement signal, a respiratory rate signal, and a brain wave signal.

In the embodiment, the processor 110 may analyze the physiological characteristic signal 102 and output a corresponding control signal 103 to the controller 131 of the projection device 130. The processor 110 may analyze the physiological characteristic signal 102 or sum up a characteristic curve of the human body state within a certain period of time, and then the current state of the sensed target is determined to be one out of a general state, a prepare-for-sleep state, a deep sleep state, and a prepare-to-wake-up state. Moreover, the processor 110 may control the projection device 130 to perform corresponding operations according to the current state of the sensed target. The control signal 103 may be a prepare-for-sleep mode control signal, a deep sleep mode control signal, or a prepare-to-wake-up mode control signal.

In the embodiment, the sleep stage of the sensed target may include a prepare-for-sleep stage, a deep sleep stage, and a prepare-to-wake-up stage, for example. Therefore, the processor 110 may determine the sleep stage of the sensed target according to an analysis result of the physiological characteristic signal 102 to decide to output a prepare-for-sleep mode control signal, a deep sleep mode control signal, or a prepare-to-wake-up mode control signal, for example, to the controller 131 of the projection device 130. The controller 131 may control the projection device 130 to execute the prepare-for-sleep mode, the deep sleep mode, or the prepare-to-wake-up mode to adjust the corresponding projection image and audio playback effect. The controller 131 may operate the projection module 132 and the audio player 133 according to the control signal 103.

In the embodiment, for example, the processor 110 and the physiological characteristic sensing device 120 may be disposed in a portable electronic device, such as a smart phone, a smart watch, a smart bracelet, or a smart clothing, and the like; but the type of electronic device is not limited in the disclosure. The portable electronic device may communicate with the projection device 130 wirelessly. Accordingly, the sensed target may carry/wear the portable electronic device, and the portable electronic device may automatically and instantly sense the physiological information of the sensed target and transmit the correspondingly generated control signal 103 to the projection device 130 in a wireless or a wired manner. Specifically, the projection device 130 has an application program that may read the control signal 103 so that the projection device 130 may perform corresponding operations. In an embodiment, the processor 110 and the physiological characteristic sensing device 120 may also be integrated in the projection device 130. The physiological characteristic sensing device 120 may sense the physiological information of the sensed target in a non-contact remote measurement manner. For example, the physiological characteristic sensing device 120 may be an image sensor. The physiological characteristic sensing device 120 may sense multiple consecutive images of blood vessels of the sensed target and may analyze the changes of multiple consecutive images of blood vessels to output a corresponding heartbeat characteristic signal to the processor 110. In another embodiment, the processor 110 may be integrated in the controller 131 of the projection device 130, and the physiological characteristic sensing device 120 may be disposed in a portable electronic device. In another embodiment, the physiological characteristic sensing device 120 may be disposed in a portable electronic device, and the processor 110 may be disposed in a host device (e.g., a computer host, a tablet computer, and the like.). The portable electronic device communicates with the host device wirelessly, and the host device communicates with the projection device 130 wirelessly.

In the embodiment, the processor 110 and the controller 131 may respectively include a central processing unit (CPU) with related data calculation functions and projection control functions, or other programmable general-purpose or special-purpose microprocessors, digital signal processors (DSPs), an image processing unit (IPU), a graphics processing unit (GPU), a programmable controller, application specific integrated circuits (ASICs), a programmable logic device (PLD), other similar control devices, or a combination thereof.

In the embodiment, the projection device 130 may further include memory, the memory may be, for example, random access memory (RAM), read-only memory (ROM), flash memory, similar components, or a combination of thereof.

The memory may be used to store related projection image data, audio data, projection control programs, audio playback programs, etc., for the controller 131 to access and execute.

In the embodiment, the projection module 132 may include a projection light source, an optical engine, and an optical system. The projection light source may include a light emitting unit such as a discharge bulb, a light emitting diode, or a laser light source. The optical engine may include a reflective spatial light modulation device or a transmissive spatial light modulation device. The reflective spatial light modulation device may include reflective liquid crystals on silicon (LCOS) or a digital micro-mirror device (DMD), for example. The transmissive spatial light modulation device may include a transparent liquid crystal panel, for example. The optical system may include multiple lenses, and the multiple lenses may be disposed on the optical path of the projection beam. In the embodiment, the audio player 133 may include a speaker.

Moreover, in some embodiments of the disclosure, the projection system 100 may not include the processor 110 and the physiological characteristic sensing device 120. Accordingly, the projection device 130 may automatically execute the prepare-for-sleep mode, the deep sleep mode, or the prepare-to-wake-up mode according to a predetermined time set by the user.

Figure 2:
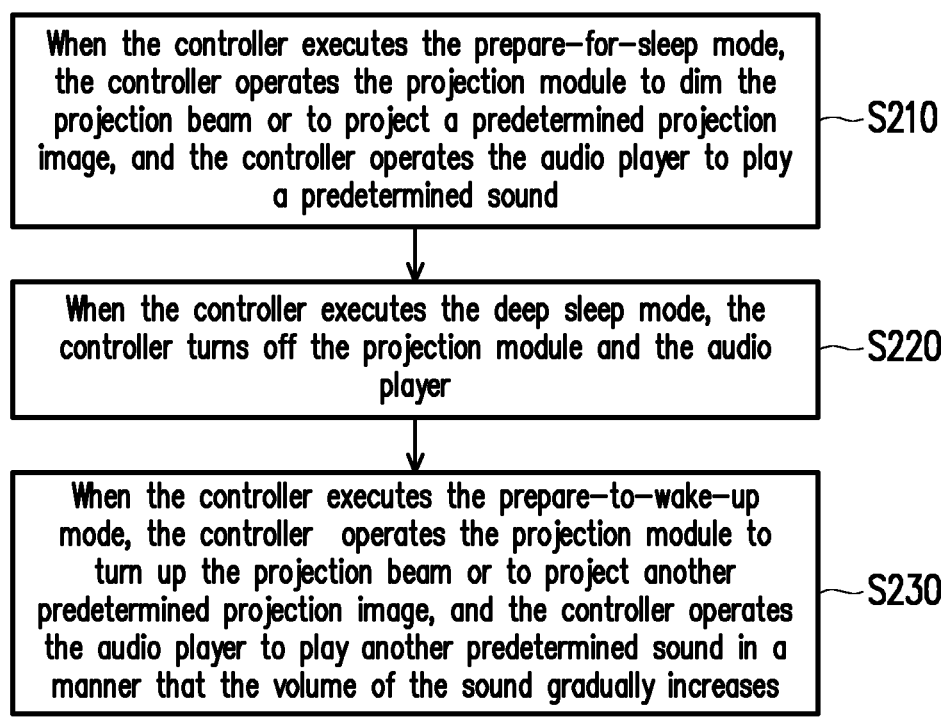
FIG. 2 is a flowchart of a projection method according to an embodiment of the disclosure.

FIG. 2 is a flowchart of a projection method according to an embodiment of the disclosure. Referring to FIG. 1 and FIG. 2, the projection system 100 may perform the following steps S210 to S230 to perform operations of automatic projection and audio playing. Note that in some implementation scenarios of the disclosure, merely at least one of the following steps S210 to S230 may be executed. In the embodiment, when the processor 110 determines that the current sleep stage of the sensed target is the prepare-for-sleep stage according to the physiological characteristic signal 102 provided by the physiological characteristic sensing device 120, the processor 110 may output the prepare-for-sleep mode control signal to the controller 131 so that the controller 131 executes the prepare-for-sleep mode. Alternatively, the controller 131 may execute the prepare-for-sleep mode according to a predetermined time set in advance. Alternatively, the projection device 130 may further include a light sensor.

The light sensor is coupled to the controller 131. When the sky gets darker, the light sensor may provide an ambient light sensing signal to the controller 131 according to the gradual decrease of the ambient brightness, so that the controller 131 decides to execute the prepare-for-sleep mode according to the ambient light sensing signal. Therefore, in step S210, when the controller 131 executes the prepare-for-sleep mode, the controller 131 of the projection device 130 operates the projection module 132 to dim the projection beam (decrease the intensity of the projection beam) or to project a predetermined projection image, and the controller 131 operates the audio player 133 to play a predetermined sound. In other words, when the heartbeat, respiratory rate, and/or brain wave activity of the sensed target decreases, the projection device 130 may automatically operate the projection module 132 to project a predetermined projection image that helps prepare-for-sleep and operate the audio player 133 to play the predetermined audio that helps prepare-for-sleep. Moreover, in some embodiments of the disclosure, the projection module 132 further includes a fan F. When the controller 131 executes the prepare-for-sleep mode, the controller 131 may also increase the speed of the fan E accordingly. The purpose of increasing the speed of the fan F is to increase the fan noise, the fan noise is relatively stable continuous noise that people are easy to get used to and ignore, and this relatively loud fan noise is used to cover other discontinuous noise that people are not easy to get used to and ignore (e.g., noise of falling objects upstairs, sudden knocking, or dog barking . . . etc.), so that people are less susceptible to the shock incurred by the discontinuous noise, which has negative effects on sleep.

Next, when the processor 110 determines that the current sleep stage of the sensed target is the deep sleep stage according to the physiological characteristic signal 102 provided by the physiological characteristic sensing device 120, the processor 110 may output a deep sleep mode control signal to the controller 131 so that the controller 131 executes the deep sleep mode. Alternatively, the controller 131 may execute the deep sleep mode according to another predetermined time preset by the user. Therefore, in step S220, when the controller 131 executes the deep sleep mode, the controller 131 of the projection device 130 turns off the projection module 132 and the audio player 133. In other words, when the heartbeat, respiratory rate, and/or brain wave activity of the sensed target is in a state corresponding to the deep sleep stage, the projection device 130 may automatically turn off the projection module 132 and the audio player 133.

Next, when the processor 110 determines that the current sleep stage of the sensed target is the prepare-to-wake-up state stage according to the physiological characteristic signal 102 provided by the physiological characteristic sensing device 120, the processor 110 may output the prepare-to-wake-up mode control signal to the controller 131 so that the controller 131 executes the prepare-to-wake-up mode. Alternatively, the controller 131 may execute the prepare-to-wake-up mode according to another predetermined time set in advance. Alternatively, the projection device 130 may further include a light sensor. The light sensor is coupled to the controller 131. When the sky gets brighter, the light sensor may provide an ambient light sensing signal to the controller 131 according to the gradual increase of the ambient brightness so that the controller 131 decides to execute the prepare-to-wake-up mode according to the ambient light sensing signal. Therefore, in step S230, when the controller 131 executes the prepare-to-wake-up mode, the controller 131 operates the projection module 132 to turn up the projection beam (increase the intensity of the projection beam) or to project another predetermined projection image, and the controller 131 operates the audio player 133 to play another predetermined sound in a manner that the volume of the sound gradually increases. In other words, when the heartbeat, respiratory rate, and/or brain wave activity of the sensed target gradually increases to a state corresponding to the prepare-to-wake-up stage, the projection device 130 may automatically turn on the projection module 132 and the audio player 133, the controller 131 may operate the projection module 132 to turn up the projection beam or to project another predetermined projection image, and the audio player 133 is operated to play another predetermined sound in a manner that the volume of the sound gradually increases. Therefore, the projection system 100 of the embodiment may provide an adaptive audio-visual playing function according to the sleep stage of the sensed target. Moreover, in some embodiments of the disclosure, when the controller 131 executes the prepare-to-wake-up mode, the controller 131 may also increase the speed of the fan F of the projection module 132 accordingly.

Figure 3A:
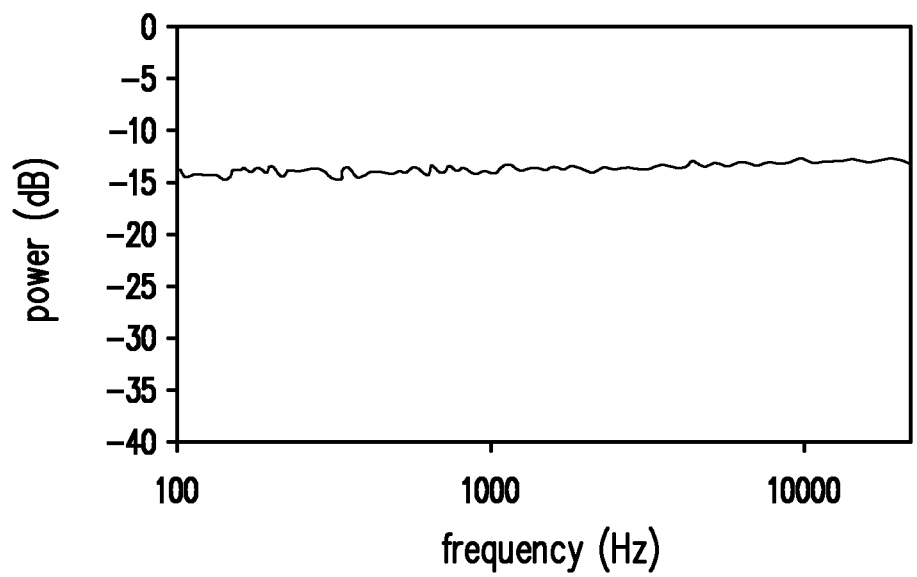
FIG. 3A is a schematic view of an approximate power spectrum of white noise according to an embodiment of the disclosure.
Figure 3B:
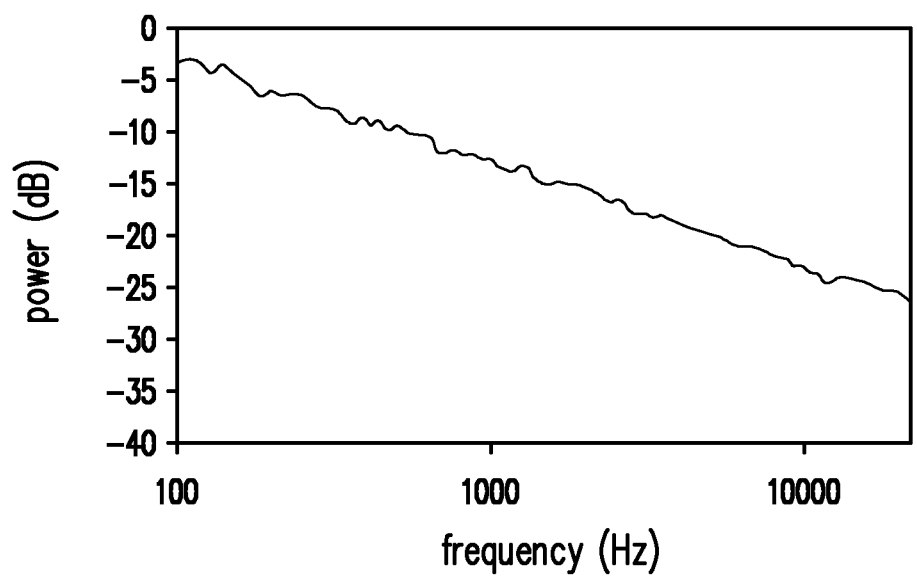
FIG. 3B is a schematic view of an approximate power spectrum of pink noise according to an embodiment of the disclosure.

In the embodiment, the predetermined sound may be white noise, pink noise, or sleep aid music, and the audio data of the white noise, pink noise or sleep aid music may be pre-stored in the projection device 130 or provided by an electronic device (e.g., the portable electronic device), the electronic device communicates with the projection device 130 wirelessly. With reference to FIG. 3A, FIG. 3A is a schematic view of an approximate power spectrum of white noise according to an embodiment of the disclosure. In the embodiment, the audio player 133 may continuously play white noise with an approximate power spectrum as shown in FIG. 3A. Alternatively, with reference to FIG. 3B, FIG. 3B is a schematic view of an approximate power spectrum of pink noise according to an embodiment of the disclosure. In the embodiment, the audio player 133 may also continuously play pink noise with an approximate power spectrum as shown in FIG. 3B.

Figure 4A:
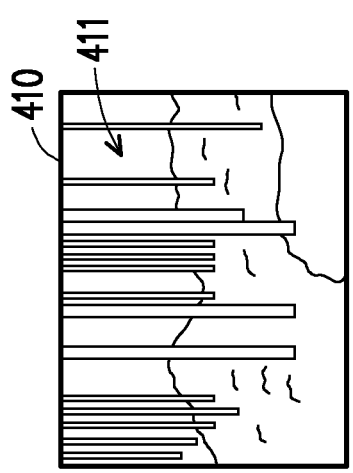
FIG. 4A is a schematic view of a first projection image according to an embodiment of the disclosure.
Figure 4B:
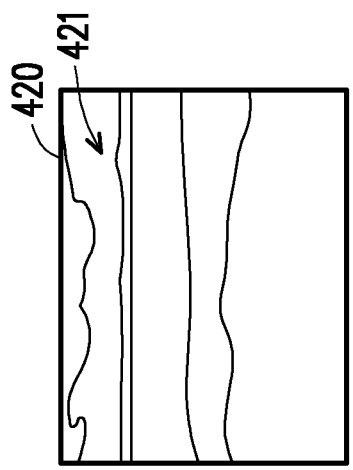
FIG. 4B is a schematic view of a second projection image according to an embodiment of the disclosure.
Figure 4C:
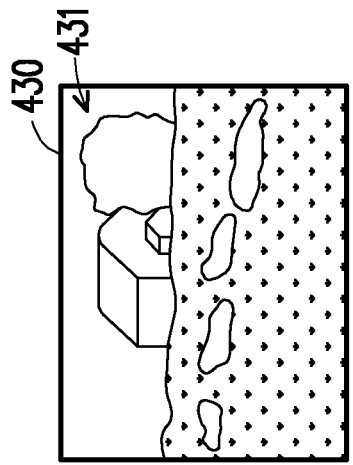
FIG. 4C is a schematic view of a third projection image according to an embodiment of the disclosure.
Figure 4D:
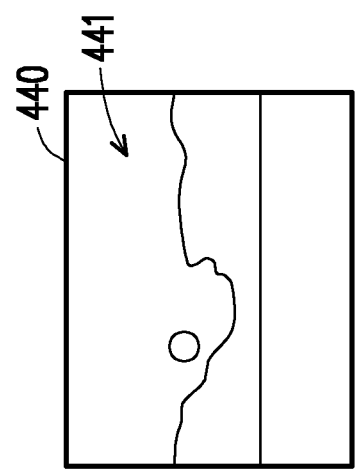
FIG. 4D is a schematic view of a fourth projection image according to an embodiment of the disclosure.
Figure 4E:
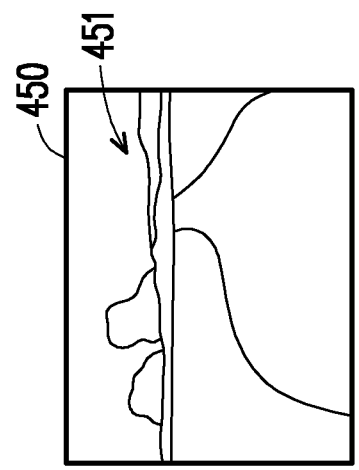
FIG. 4E is a schematic view of a fifth projection image according to an embodiment of the disclosure.
Figure 4F:
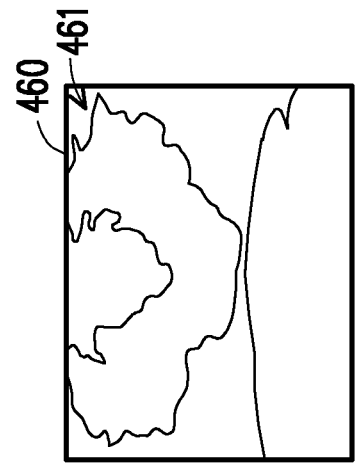
FIG. 4F is a schematic view of a sixth projection image according to an embodiment of the disclosure.

Alternatively, in some embodiments of the disclosure, referring to FIG. 4A to FIG. 4F, FIG. 4A to FIG. 4F are schematic views of the first to sixth projection images according to an embodiment of the disclosure. For example, the audio player 133 may play forest ambient sounds or forest background music, and the projection module 132 may project a predetermined projection image 410 as shown in FIG. 4A, where the predetermined projection image 410 includes a forest image 411. The audio player 133 may play ocean ambient sounds or ocean background music, and the projection module 132 may project a predetermined projection image 420 as shown in FIG. 4B, where the predetermined projection image 420 includes an ocean image 421. The audio player 133 may play rural ambient sounds or rural background music, and the projection module 132 may project a predetermined projection image 430 as shown in FIG. 4C, where the predetermined projection image 430 includes a rural image 431. The audio player 133 may play rain ambient sounds or rain background music, and the projection module 132 may project a predetermined projection image 440 as shown in FIG. 4D, where the predetermined projection image 440 includes a rain background image 441. The audio player 133 may play river ambient sounds or river background music, and the projection module 132 may project a predetermined projection image 450 as shown in FIG. 4E, where the predetermined projection image 450 includes a river background image 451. The audio player 133 may play underwater ambient sounds or underwater background music, and the projection module 132 may project a predetermined projection image 460 as shown in FIG. 4F, where the predetermined projection image 460 includes an underwater background image 461. The predetermined projection images 410 to 460 may be low-brightness projection images. Moreover, the audio player 133 may also automatically generate at least one of forest ambient sounds, ocean ambient sounds, rural ambient sounds, rain ambient sounds, river ambient sounds and underwater ambient sounds based on the playlist set by the user or based on the user's historical preferences, and the projection module 132 may also automatically play back at least one of the predetermined projection images 410 to 460.

Figure 5A:
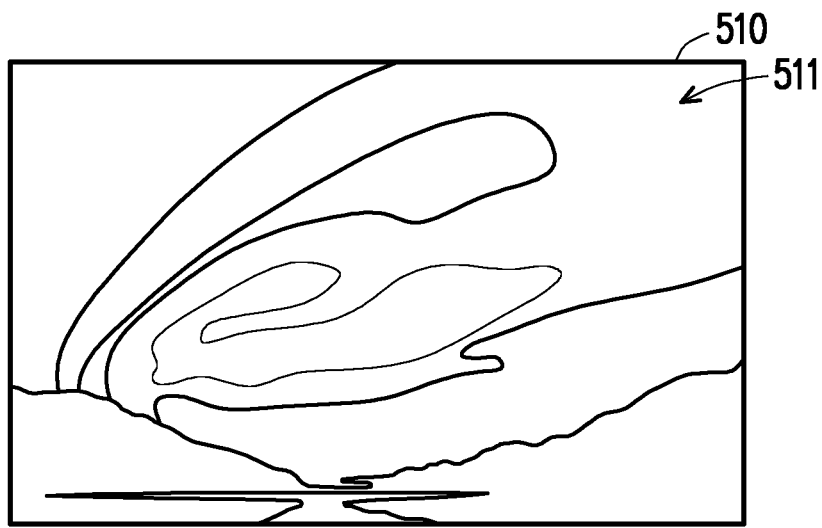
FIG. 5A is a schematic view of a projection image with a specific wavelength according to an embodiment of the disclosure.
Figure 5B:
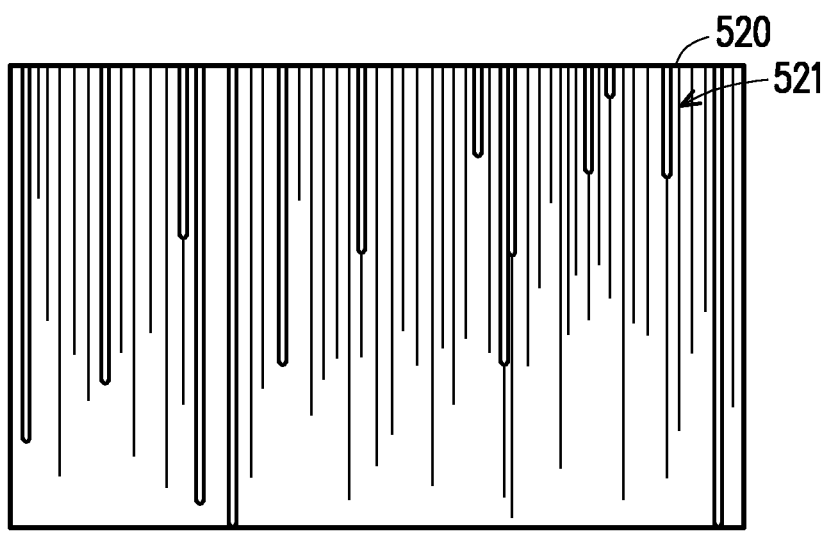
FIG. 5B is a schematic view of a projection image with a specific color temperature according to an embodiment of the disclosure.

Alternatively, in other embodiments of the disclosure, referring to FIG. 5A and FIG. 5B, FIG. 5A is a schematic view of a projection image with a specific wavelength according to an embodiment of the disclosure, and FIG. 5B is a schematic view of a projection image with a specific color temperature according to an embodiment of the disclosure. For example, the projection module 132 may automatically play a predetermined projection image 510 with a specific wavelength as shown in FIG. 5A. The projection image 511 of the predetermined projection image 510 may be a green light-based image content, such as an aurora image, to provide soft light, for example. Alternatively, it is a predetermined projection image 520 with a specific color temperature as shown in FIG. 5B. For example, the projection image 521 of the predetermined projection image 520 may be an image content mainly composed of low-brightness warm-color light, such as a light stripe variable image, to provide low-stimulus light. In other words, the projection system 100 may automatically create a projection situation contributing to falling prepare-for-sleep stage or deep-sleep stage of the sensed targets.

Moreover, the number of the sensed targets is not limited to one. In some embodiments of the disclosure, the projection system 100 may further include another physiological characteristic sensing device 120A. Another physiological characteristic sensing device 120A may be used to obtain another physiological information 101A to generate another physiological characteristic signal 102A. The processor 110 may analyze another physiological characteristic signal 102A and output a prepare-for-sleep mode control signal, a deep sleep mode control signal, or a prepare-to-wake-up mode control signal to the projection device 130 according to the physiological characteristic signal 102 and the another physiological characteristic signal 102A. In other words, the projection system 100 may comprehensively evaluate the states of multiple sensed targets to control the projection device 130 to perform corresponding projection and audio playing.

Moreover, in some embodiments of the disclosure, the processor 110 may also output a warning signal to the projection device 130 according to whether the physiological characteristic signal is abnormal, so that the projection device 130 may operate at least one of the projection module 132 and the audio player 133 to play the warning message. In other words, the physiological characteristic sensing device 120 continuously senses the physiological information of the sensed target, so it may be applied to health and personal safety monitoring. For example, hazards such as fire smoke or gas leakage which results in too low or too high heartbeat and/or respiratory rate of the sensed target. Accordingly, the processor 110 may also determine whether to issue a warning through the projection device 130 according to whether the physiological characteristic signal is greater than a first preset value or less than a second preset value.

In an implementation scenario of the disclosure, multiple operation modes may be further distinguished among the above multiple modes, and the disclosure is not limited thereto. For example, before the sensed target going to sleep, when the processor 110 determines that time has reached the first predetermined time (or time according to the sleep habit of the sensed target), the processor 110 may provide a corresponding first control signal to the controller 131, so that the controller 131 may operate the projection module 132 to project a predetermined projection image to remind the sensed target to prepare for sleep. Next, when the sensed target is about to fall asleep, and the processor 110 determines that time has reached the second predetermined time (or time according to the sleep habit of the sensed target), the processor 110 may provide a corresponding second control signal to the controller 131, so that the controller 131 may operate the projection module 132 to project a predetermined projection image and operate the audio player 133 to play white noise, pink noise, or a predetermined sound. Alternatively, the controller 131 may adjust the speed of the fan F of the projection module 132 from a first speed to a second speed. Then, during sleep, when the processor 110 determines that time has reached the third predetermined time (or time according to the sleep habit of the sensed target), the processor 110 may provide a corresponding third control signal to the controller 131, so that the controller 131 may dim the projection brightness of the projection module 132. Alternatively, the controller 131 may adjust the volume of the white noise or the pink noise from the first volume increased to the second volume.

Then, during light sleep, when the processor 110 determines that time has reached a fourth predetermined time (or according to the sleep habit of the sensed target), the processor 110 may provide a corresponding fourth control signal to the controller 131, so that the controller 131 may simultaneously or non-simultaneously dim the projection brightness of the projection module 132 and reduce the volume of the white noise, pink noise, or predetermined sound played by the audio player 133. It should be noted that in each of the "about to fall asleep", "during sleep", "during light sleep" mentioned above, the processor 110 may control the projection device 130 to dim the projection beam (e.g., reduce the intensity of the projection beam), project a predetermined projection image, or adjust a volume of a predetermined sound played by the audio player 133. In addition, the terms of "about to fall asleep", "during sleep", "during light sleep" corresponds to the prepare-for-sleep stage of the sensed target. Then, during deep sleep stage, when the processor 110 determines that time has reached a fifth predetermined time (or time according to the sleep habit of the sensed target), the processor 110 may provide a corresponding fifth control signal to the controller 131, so that the controller 131 may turn off the projection module 132 and audio player 133. Finally, during the prepare-to-wake-up stage, when the processor 110 determines that time has reached a sixth predetermined time (or time according to the sleep habit of the sensed target), the processor 110 may provide a corresponding sixth control signal to the controller 131, so that the controller 131 may simultaneously or non-simultaneously turn on the projection module 132 and the audio player 133.

Based on the above, with the projection system and the projection method of the disclosure, the physiological characteristic information of the sensed target may be continuously sensed and the projection beam or the projection image may be automatically adjusted according to the change of the physiological characteristic information of the sensed target. With the projection system and the projection method of the disclosure and by projecting a predetermined projection image and/or playing a predetermined audio, an audio-visual situation that helps the sensed target prepare to fall asleep and/or sleep may be automatically created, and the sleep quality of the sensed target may be progressively maintained. Moreover, with the projection system and projection method of the disclosure, the sensed target may also be automatically woken up. Moreover, with the projection system and projection method of the disclosure, the physiological characteristic information of the sensed target may be further monitored to provide a practical warning function.

The foregoing description of the preferred of the disclosure has been presented for purposes of illustration and description. It is not intended to be exhaustive or to limit the disclosure to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the disclosure and its best mode practical application, thereby to enable persons skilled in the art to understand the disclosure for various embodiments and with various modifications as are suited to the particular use or implementation contemplated. It is intended that the scope of the disclosure be defined by the claims appended hereto and their equivalents in which all terms are meant in their broadest reasonable sense unless otherwise indicated. Therefore, the term "the disclosure", "the disclosure" or the like does not necessarily limit the claim scope to a specific embodiment, and the reference to particularly preferred exemplary embodiments of the disclosure does not imply a limitation on the disclosure, and no such limitation is to be inferred. The disclosure is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the disclosure. It should be appreciated that variations may be made in the embodiments described by persons skilled in the art without departing from the scope of the disclosure as defined by the following claims. Moreover, no element and component in the disclosure is intended to be dedicated to the public regardless of whether the element or component is explicitly recited in the following claims.

What is claimed is:

1. A projection system, wherein the projection system comprises a projection device,
    the projection device comprises a projection module, a controller, and an audio player, wherein
    the projection module comprises a fan;
    the controller is coupled to the projection module; and
    the audio player is coupled to the controller,
    wherein when the controller executes a prepare-for-sleep mode, the controller is configured to:
        operate the projection module to dim a projection beam or to project a predetermined projection image;
        increase a speed of the fan from a first speed to a second speed so as to increase a fan noise of the fan and continuously provide the fan noise for preparing for sleep; and
        operate the audio player to play a predetermined sound.

2. The projection system according to claim 1, wherein when the controller executes a deep sleep mode, the controller is configured to turn off the projection module and the audio player.

3. The projection system according to claim 2, wherein when the controller executes a prepare-to-wake-up mode, the controller is configured to operate the projection module to turn up the projection beam or to project another predetermined projection image and operate the audio player to play another predetermined sound in a manner that a volume of the sound gradually increases.

4. The projection system according to claim 3, wherein the controller is configured to execute the prepare-for-sleep mode, the deep sleep mode, and the prepare-to-wake-up mode according to three periods of predetermined time.

5. The projection system according to claim 3, wherein the projection device further comprises:
a light sensor coupled to the controller and adapted to provide an ambient light sensing signal, wherein the controller is configured to select and execute the prepare-for-sleep mode or the prepare-to-wake-up mode according to the ambient light sensing signal.

6. The projection system according to claim 3, wherein when the controller executes the prepare-to-wake-up mode, the controller adjusts the speed of the fan of the projection module.

7. The projection system according to claim 1, wherein the predetermined sound is white noise, pink noise, or sleep aid music; wherein audio data of the white noise, the pink noise, or the sleep aid music are pre-stored in the projection device or provided by an electronic device; and the electronic device communicates with the projection device wirelessly.

8. The projection system according to claim 1, wherein the predetermined projection image comprises at least one of a specific wavelength and a specific color temperature.

9. A projection method, wherein the projection method is adapted for a projection system, the projection system comprises a projection device, and the projection device comprises a projection module, a controller, and an audio player, wherein the projection module comprises a fan, and the projection method comprises:
when the controller executes a prepare-for-sleep mode,
operating the projection module by the controller to dim a projection beam or to project a predetermined projection image;
increasing a speed of the fan from a first speed to a second speed by the controller so as to increase a fan noise of the fan and continuously provide the fan noise for preparing for sleep; and
operating the audio player by the controller to play a predetermined sound.

10. The projection method according to claim 9, wherein the projection method further comprises:
when the controller executes a deep sleep mode,
turning off the projection module and the audio player by the controller.

11. The projection method according to claim 10, wherein the projection method further comprises:
when the controller executes a prepare-to-wake-up mode,
operating the projection module by the controller to turn up the projection beam or to project another predetermined projection image; and
operating the audio player by the controller to play another predetermined sound in a manner that a volume of the sound gradually increases.

12. The projection method according to claim 11, wherein the controller executes the prepare-for-sleep mode, the deep sleep mode, and the prepare-to-wake-up mode according to three periods of predetermined time.

13. The projection method according to claim 11, wherein the projection device further comprises a light sensor, wherein the light sensor provides an ambient light sensing signal so that the controller selects and executes the prepare-for-sleep mode or the prepare-to-wake-up mode according to the ambient light sensing signal.

14. The projection method according to claim 11, wherein the projection method further comprises:
when the controller executes the prepare-to-wake-up mode, adjusting the speed of the fan of the projection module by the controller.

15. The projection method according to claim 9, wherein the predetermined sound is white noise, pink noise, or sleep aid music; wherein audio data of the white noise, the pink noise, or the sleep aid music are pre-stored in the projection device or provided by an electronic device; and the electronic device communicates with the projection device wirelessly.

16. The projection method according to claim 9, wherein the predetermined projection image comprises at least one of a specific wavelength and a specific color temperature.

17. A projection system, wherein the projection system comprises a projection device,
the projection device comprises a projection module, a controller, and an audio player, wherein
the controller is coupled to the projection module; and the audio player is coupled to the controller,
wherein when the controller executes a prepare-for-sleep mode, the controller is configured to operate the projection module to dim a projection beam or to project a predetermined projection image and operate the audio player to play a predetermined sound,
wherein when the controller executes a deep sleep mode, the controller is configured to turn off the projection module and the audio player,
wherein when the controller executes a prepare-to-wake-up mode, the controller is configured to operate the projection module to turn up the projection beam or to project another predetermined projection image and operate the audio player to play another predetermined sound in a manner that a volume of the sound gradually increases,
wherein the projection system further comprises a physiological characteristic sensing device and a processor, wherein
the physiological characteristic sensing device is adapted to obtain a physiological characteristic signal; and
the processor is coupled to the physiological characteristic sensing device and adapted to analyze the physiological characteristic signal,
wherein the processor is configured to output one of a prepare-for-sleep mode control signal, a deep sleep mode control signal, and a prepare-to-wake-up mode control signal to the projection device according to the physiological characteristic signal, so that the controller executes the prepare-for-sleep mode, the deep sleep mode, and the prepare-to-wake-up mode according to the one of the prepare-for-sleep mode control signal, the deep sleep mode control signal, and the prepare-to-wake-up mode control signal.

18. The projection system according to claim 17, wherein the physiological characteristic sensing device and the processor are disposed in a portable electronic device, and the portable electronic device communicates with the projection device wirelessly.

19. The projection system according to claim 17, wherein the physiological characteristic sensing device is disposed in a portable electronic device, and the controller comprises the processor, wherein the portable electronic device communicates with the projection device wirelessly.

20. The projection system according to claim 17, wherein the physiological characteristic sensing device is disposed in a portable electronic device, the processor is disposed in a host device, the portable electronic device communicates with the host device wirelessly, and the host device communicates with the projection device wirelessly.

21. The projection system according to claim 17, wherein the physiological characteristic signal comprises at least one of a heartbeat signal, a pulse signal, an eye movement signal, a respiratory rate signal, and a brain wave signal.

22. The projection system according to claim 17, wherein the projection system further comprises:
another physiological characteristic sensing device adapted to obtain another physiological information to generate another physiological characteristic signal, wherein the processor analyzes the another physiological characteristic signal,
wherein the processor is configured to output another one of the prepare-for-sleep mode control signal, the deep sleep mode control signal, and the prepare-to-wake-up mode control signal to the projection device according to the physiological characteristic signal and the another physiological characteristic signal.

23. The projection system according to claim 17, wherein the processor is further configured to output a warning signal to the projection device according to whether the physiological characteristic signal is abnormal, so that the projection device operates at least one of the projection module and the audio player to play a warning message.

24. A projection method, wherein the projection method is adapted for a projection system, the projection system comprises a projection device, and the projection device comprises a projection module, a controller, and an audio player, wherein the projection method comprises:
when the controller executes a prepare-for-sleep mode,
operating the projection module by the controller to dim a projection beam or to project a predetermined projection image; and
operating the audio player by the controller to play a predetermined sound,
wherein the projection method further comprises:
when the controller executes a deep sleep mode, turning off the projection module and the audio player by the controller;
when the controller executes a prepare-to-wake-up mode,
operating the projection module by the controller to turn up the projection beam or to project another predetermined projection image; and
operating the audio player by the controller to play another predetermined sound in a manner that a volume of the sound gradually increases,
wherein the projection system further comprises a physiological characteristic sensing device and a processor, and the projection method further comprises:
obtaining a physiological characteristic signal by the physiological characteristic sensing device;
analyzing the physiological characteristic signal by the processor;
outputting one of a prepare-for-sleep mode control signal, a deep sleep mode control signal, and a prepare-to-wake-up mode control signal to the projection device by the processor according to the physiological characteristic signal; and
correspondingly executing the prepare-for-sleep mode, the deep sleep mode, or the prepare-to-wake-up mode by the controller according to the prepare-for-sleep mode control signal, the deep sleep mode control signal, or the prepare-to-wake-up mode control signal, respectively.

25. The projection method according to claim 24, wherein the physiological characteristic sensing device and the processor are disposed in a portable electronic device, and the portable electronic device communicates with the projection device wirelessly.

26. The projection method according to claim 24, wherein the physiological characteristic sensing device is disposed in a portable electronic device, and the controller comprises the processor, wherein the portable electronic device communicates with the projection device wirelessly.

27. The projection method according to claim 24, wherein the physiological characteristic sensing device is disposed in a portable electronic device, the processor is disposed in a host device, the portable electronic device communicates with the host device wirelessly, and the host device communicates with the projection device wirelessly.

28. The projection method according to claim 24, wherein the physiological characteristic signal comprises at least one of a heartbeat signal, a pulse signal, an eye movement signal, a respiratory rate signal, and a brain wave signal.

29. The projection method according to claim 24, wherein the projection system further comprises another physiological characteristic sensing device, and the projection method further comprises:
obtaining another physiological information by the another physiological characteristic sensing device to generate another physiological characteristic signal;
analyzing the another physiological characteristic signal by the processor; and
outputting another one of the prepare-for-sleep mode control signal, the deep sleep mode control signal, and the prepare-to-wake-up mode control signal to the projection device by the processor according to the physiological characteristic signal and the another physiological characteristic signal.

30. The projection method according to claim 24, wherein the projection method further comprises:
outputting a warning signal to the projection device by the processor according to whether the physiological characteristic signal is abnormal, so that the projection device operates at least one of the projection module and the audio player to play a warning message.

* * * * *